(12) United States Patent
Anderson

(10) Patent No.: US 9,730,728 B2
(45) Date of Patent: Aug. 15, 2017

(54) UNIVERSAL BELLOWS

(71) Applicant: Robert G. Anderson, Aledo, TX (US)

(72) Inventor: Robert G. Anderson, Aledo, TX (US)

( * ) Notice: Subject to any disclaimer, the term of this patent is extended or adjusted under 35 U.S.C. 154(b) by 0 days.

(21) Appl. No.: 15/277,580

(22) Filed: Sep. 27, 2016

(65) Prior Publication Data

US 2017/0014158 A1    Jan. 19, 2017

Related U.S. Application Data

(62) Division of application No. 14/849,219, filed on Sep. 9, 2015, now Pat. No. 9,615,908.

(60) Provisional application No. 62/100,592, filed on Jan. 7, 2015.

(51) Int. Cl.

| | |
|---|---|
| *A61F 2/12* | (2006.01) |
| *A61B 17/34* | (2006.01) |
| *A61B 17/02* | (2006.01) |
| *A61F 2/00* | (2006.01) |
| *A61B 17/00* | (2006.01) |
| *A61B 90/40* | (2016.01) |

(52) U.S. Cl.
CPC .......... *A61B 17/3468* (2013.01); *A61B 17/02* (2013.01); *A61B 17/0293* (2013.01); *A61B 17/3423* (2013.01); *A61F 2/0095* (2013.01); *A61F 2/12* (2013.01); *A61B 90/40* (2016.02); *A61B 2017/0046* (2013.01); *A61B 2017/00796* (2013.01); *A61B 2017/3435* (2013.01)

(58) Field of Classification Search
CPC .... A61F 2/12; A61F 2250/0003; A61L 27/18; A61L 2430/04; C08L 83/04
See application file for complete search history.

(56) References Cited

U.S. PATENT DOCUMENTS

| | | | |
|---|---|---|---|
| 4,641,648 | A | 2/1987 | Shapiro |
| 4,955,906 | A | 9/1990 | Coggins et al. |
| 5,571,178 | A | 11/1996 | Ledergerber |
| 5,723,006 | A | 3/1998 | Ledergerber |
| 5,782,913 | A | 7/1998 | Schindler et al. |
| 8,206,443 | B2 | 6/2012 | Preissman |
| 8,211,173 | B2 | 7/2012 | Keller et al. |
| 8,313,760 | B2 | 11/2012 | Hunter |
| 8,550,090 | B2 | 10/2013 | Keller et al. |
| 8,555,893 | B2 | 10/2013 | Keller et al. |
| 8,641,758 | B1 | 2/2014 | Anderson |

(Continued)

FOREIGN PATENT DOCUMENTS

WO    WO/2013/122568 A1    8/2013

OTHER PUBLICATIONS

Richard A. Mladick, M.D., F.A.C.S. "No-Touch" Submuscular Saline Breast Augmentation Technique, Aesthetic Plastic Surgery, 17:183-192, 1993, New York, NY.

(Continued)

*Primary Examiner* — Thomas J Sweet
*Assistant Examiner* — Tiffany Shipmon
(74) *Attorney, Agent, or Firm* — Kirby B. Drake; Klemchuk LLP

(57) ABSTRACT

An apparatus and method for inserting prosthesis implants into a patient pocket. The apparatus includes a universal bellows, prosthesis, and a retractor. The apparatus prevents infection; eases insertion and placement; and reduces complications. In use, the retractor anchors the universal bellows to the patient while allowing the bellows to be manipulated to force the prosthesis into a surgical pocket of a patient.

1 Claim, 12 Drawing Sheets

(56) References Cited

U.S. PATENT DOCUMENTS

Figure 1:
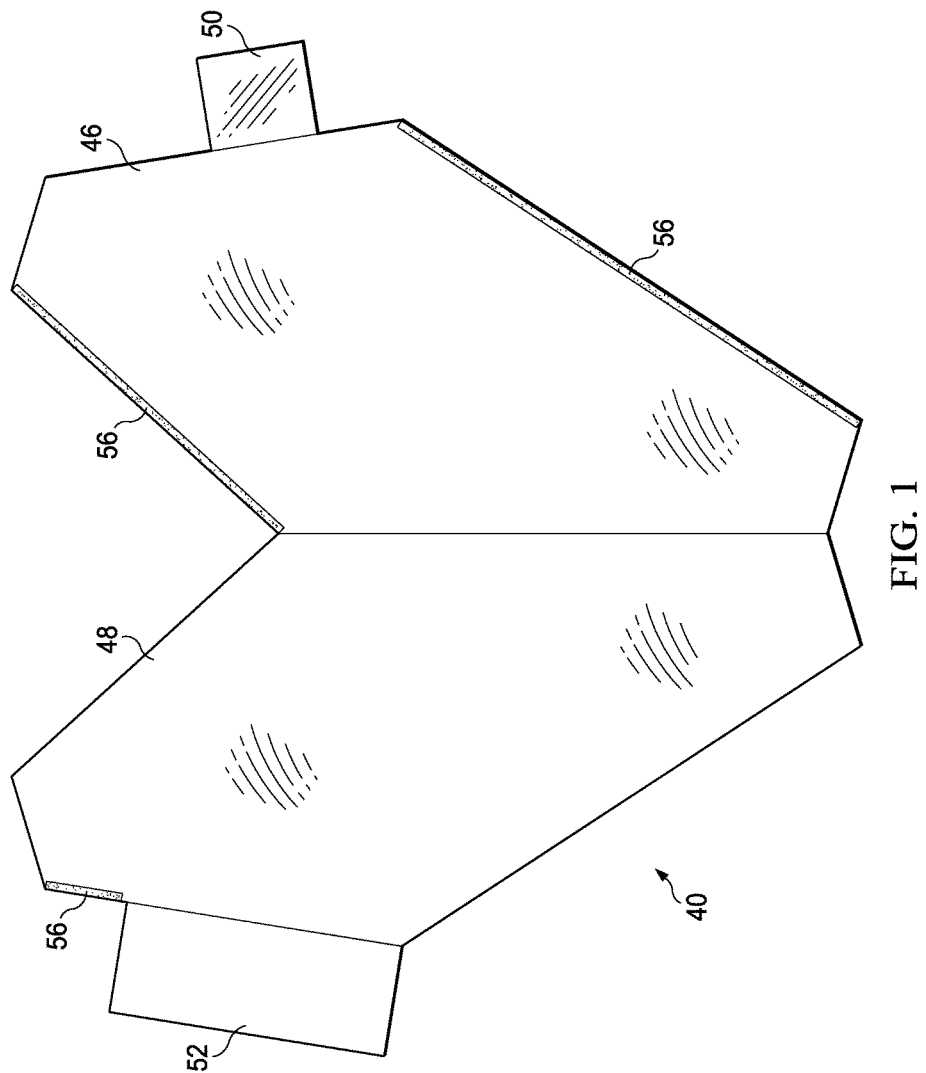

| | | |
|---|---|---|
| D736,372 S | 8/2015 | Anderson |
| D738,490 S | 9/2015 | Anderson |
| D742,509 S | 11/2015 | Anderson |
| D752,739 S | 3/2016 | Anderson |
| 2007/0276484 A1 | 11/2007 | Abell et al. |
| 2009/0204107 A1 | 8/2009 | Keller et al. |
| 2010/0280610 A1 | 11/2010 | Preissman |
| 2011/0035003 A1 | 2/2011 | Preissman |
| 2011/0218624 A1 | 9/2011 | Preissman |
| 2012/0185042 A1 | 7/2012 | Preissman |
| 2012/0259414 A1 | 10/2012 | Preissman |
| 2013/0073040 A1 | 3/2013 | Preissman |
| 2014/0074235 A1 | 3/2014 | Keller et al. |
| 2014/0074236 A1 | 3/2014 | Keller et al. |
| 2014/0148901 A1 | 5/2014 | Anderson |
| 2015/0126812 A1 | 5/2015 | Anderson |
| 2015/0374478 A1 | 12/2015 | Anderson |
| 2016/0038275 A1 | 2/2016 | Preissman |
| 2016/0095697 A1 | 4/2016 | Anderson |

OTHER PUBLICATIONS

Richard A. Mladick, M.D., F.A.C.S. Significance of *Staphylococcus epidermidis* Causing Subclinical Infection, Plastic & Reconstructive Surgery: Apr. 15, 2005—vol. 115—Issue 5—pp. 1426-1427, Virginia Beach, VA.

Richard A. Mladick, M.D., F.A.C.S. Prevention of Capsular Contracture, Plastic & Reconstructive Surgery: May 1999—vol. 103—Issue 6—pp. 1773-1774, Virginia Beach, VA.

Thomas M. Biggs, M.D. Prefilled Saline Breast Implants Offer Significant Advantages, Aesthetic Surgery Journal Sep. 1999 vol. 19 No. 5 424, St Louis, MO.

"Mitchel H. Brown, M.D.., M.Ed. Cohesive Silicone Gel Breast Implants in Aesthetic and Reconstructive Breast Surgery, Plastic & Reconstructive Surgery: Sep. 1, 2005—vol. 116—Issue 3—pp. 768-779".

UNIVERSAL BELLOWS

CROSS-REFERENCE TO RELATED APPLICATIONS

A claim of priority is made in this application based on application Ser. No. 14/849,219 filed on Sep. 9, 2015 and entitled "Universal Bellow" which further claim priority based on Provisional Application Ser. No. 62/100,592 filed on Jan. 7, 2015 and entitled "Prosthesis Implant Device" the disclosures of which are hereby incorporated by reference in its entirety.

BACKGROUND

Field of Invention

The invention related to the apparatus and method of safely inserting a prosthesis into a human body.

Background of the Invention

The present invention is a useful and novel apparatus for assisting a surgeon in avoiding complications during a prosthesis implant surgery, such as a breast implant.

Breast implants are a manufactured prosthesis used in cosmetic and reconstructive surgery. A breast implant is gelatinous, having an outer casing or membrane and an inner fluid substance such as saline or silicone.

Most implant procedures today do not use an insertion device. The surgeon makes the incision, creates a pocket for the implant, retracts the incision and then manually pushes the implant into the pocket. A saline implant can be inserted into a pocket in an empty configuration; once in place in the pocket, the implant is then filled with saline solution.

Preferably, the incision in the patient is as short as possible. Shorter incisions are less unsightly. This goal of a shorter incision is easier to accomplish with a saline implant. A saline implant is relatively easy to insert through a short incision, as the bladder is unfilled and therefore small in size as it passes through the incision. In contrast, silicone implants are prefilled resulting in a more difficult and complications-susceptible operation.

The incision is made in one of four places: under the arm, in the breast fold, in the belly button, or around the nipple. Except for the belly button insertion, one incision is made for each implant. Next, the surgeon cuts a path through the tissue to the desired destination of the implant. Once that path has been created, the tissue and muscle must be separated to create a pocket, or cavity, for the implant.

The pocket may be formed in one of two places under the breast: subglandular (between the breast tissue and pectoralis major muscle) or subpectoral (under the pectoralis major muscle). Subglandular places the prosthesis directly behind the mammary gland and in front of the muscle. Subpectoral places the implant partially under the pectoralis major muscle. Due to the structure of the pectoralis major, a portion of the implant is not covered by the pectoralis.

For inflatable implants, the surgeon rolls up the implant like a cigar and pushes it through the incision and into the pocket. The surgeon then uses a tube to fill the implant with saline.

For pre-filled implants, the procedure requires a larger incision length. The implant is then manually pushed through the incision into the pocket.

Risks to patients receiving breast implants include additional surgeries to change the placement (from subglandular to subpectoral or visa versa), or to correct folding, rupture; infection; breast pain; contracted scar tissue forming around the implant; and collections of fluids around the implant.

The overall complication rate is about 25% for silicone gel breast augmentation with the majority of re-operations related to implant rupture, leak or capsular contracture.

Infection, or Cellulitis, occurs in 2%-4% of patients, with some surgeons reporting much higher rates, and is usually from the bacteria normally present on the skin. Symptoms of infection include fever, pain, swelling and redness. To reduce infection, surgeons give a single dose of antibiotics before the surgery, and use an antibiotic solution in the wound before implant placement. The antibiotic solution may double as lubrication to allow easier insertion of the implant into the pocket. However, surgeons can bring the rate of infection down further by eliminating the chance the prosthesis touches the skin. This "no touch" technique can be improved with universal bellows of the present invention.

The implant insertion devices heretofore known suffer from a number of disadvantages:
1. Difficult to handle in a lubricious state.
2. Difficult to maintain position of insertion device in the incision.
3. Difficult to manage the speed of the insertion through the proximal end of the insertion device into the pocket.
4. Have no control over external pressure applied to implant.
5. Requires the surgeon to resize the insertion device to match different implant sizes.
6. Allow the implant to come in contact with a reusable retractor which has microscopic irregularities and/or sharp edges.
7. Due to the high cost, encourage re-use despite manufacturer recommendation not do so.

SUMMARY OF THE INVENTION

An invention, which meets the needs stated above, is a system and method to insert a prosthesis into a patient. The method allows the surgeon greater control over the insertion while reducing the chance of surgical and post-surgery complications.

Objects and Advantages

Accordingly, besides the objects and advantages of the system for a breast insertion device described above, several objects and advantages of the present invention are:
a) to provide a easier manipulation of the insertion device;
b) to provide a complication-reducing method;
c) to provide a simplified insertion method;
d) to provide a controlled minimum incision length;
e) to provide a secured proximal end to the patient;
f) to provide a safe maximum pressure applied to the breast implant.

Further objects and advantages of this invention will become apparent from a consideration of the drawings and the ensuing description of the drawings.

DRAWING FIGURES

The accompanying drawings, which are incorporated in and constitute a part of this specification, illustrate embodiments of the present invention and together with the description, serve to explain the principles of this invention. In the figures:

FIG. 1: Top view of an unassembled bellows.

Figure 2:
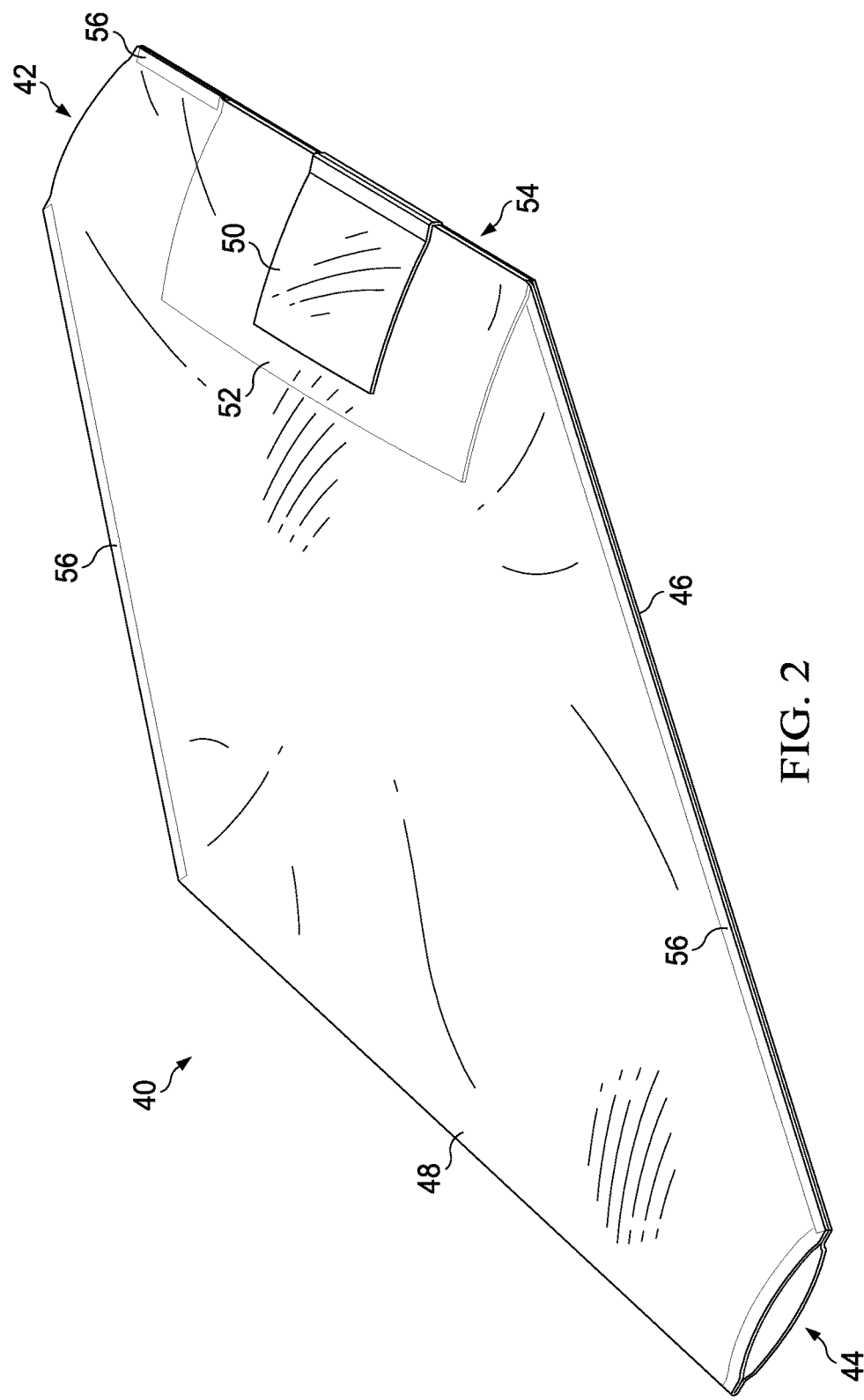

FIG. 2: Top perspective view of an assembled bellows.

Figure 3:
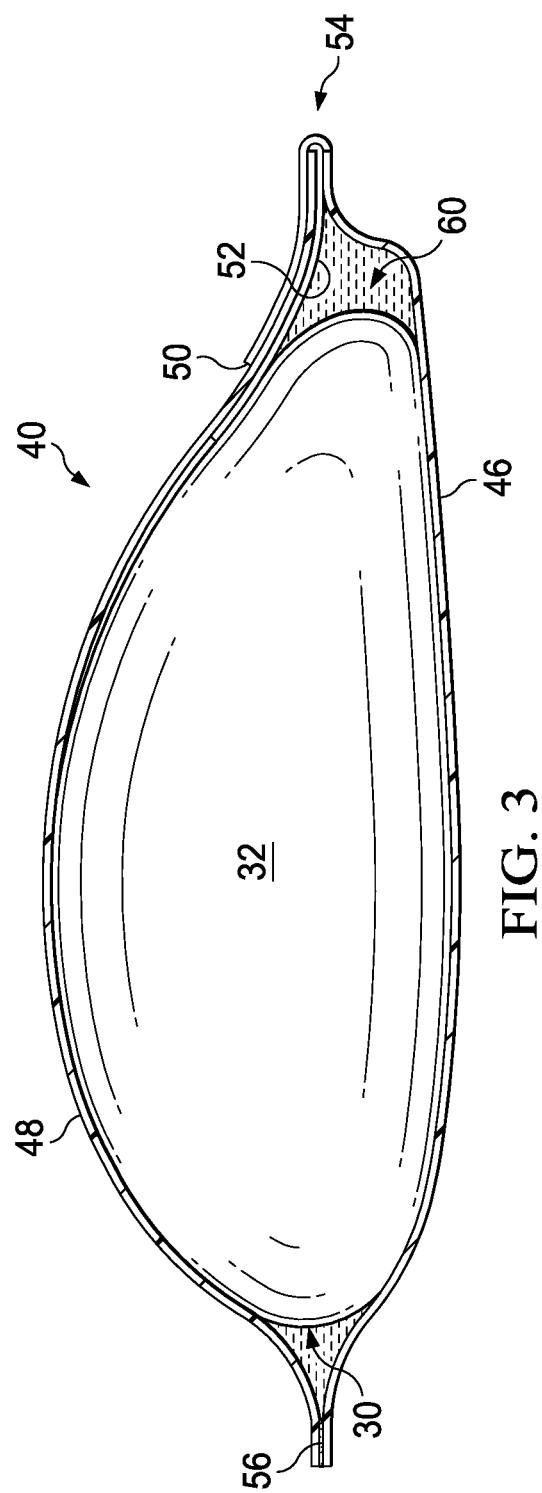

FIG. 3: Cross sectional view of an assembled bellows with an inserted prosthesis.

Figure 4:
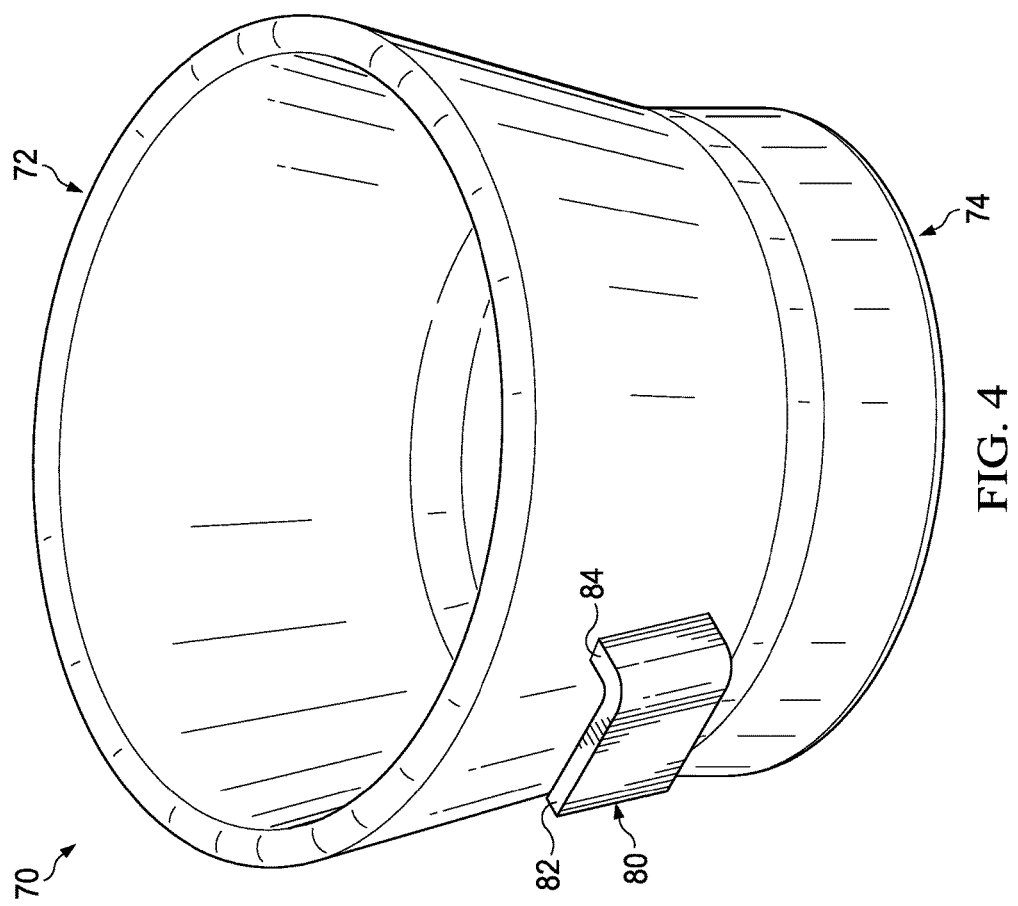

FIG. 4: Front perspective view of a universal device.

Figure 5:
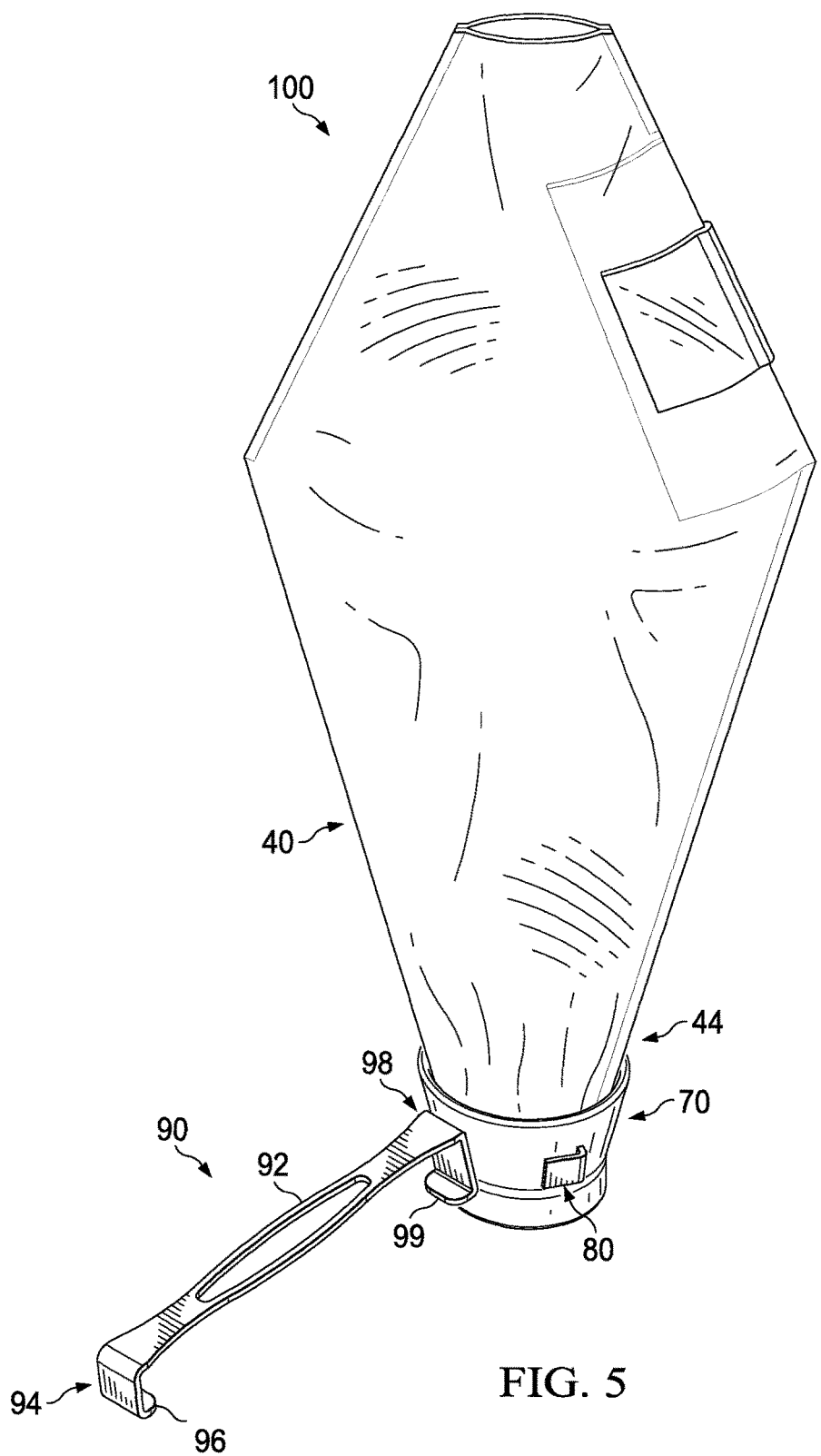

FIG. 5: Front perspective view of universal bellows before being rotated into the coupling catch.

Figure 6:
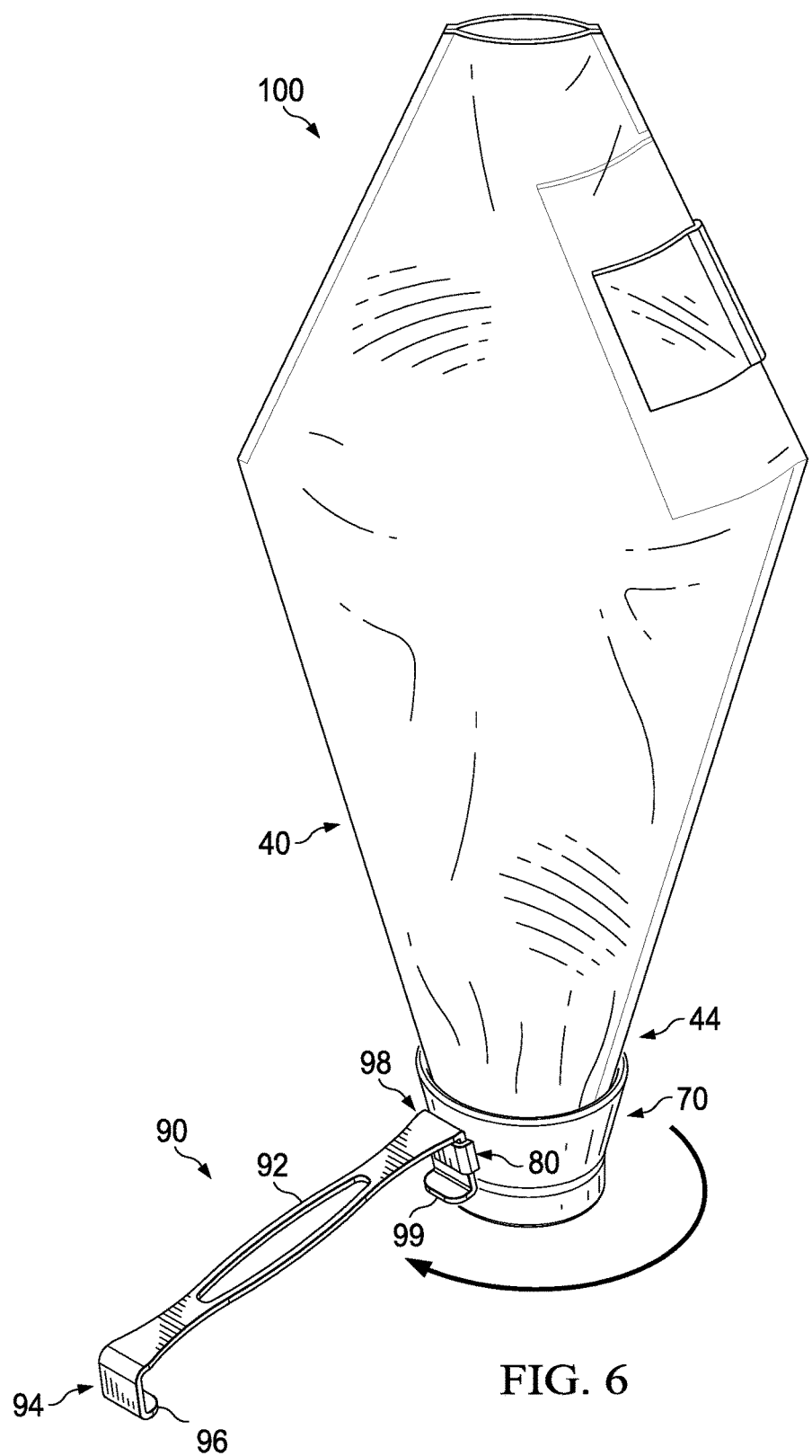

FIG. 6: Front perspective view of universal bellows after being rotated counterclockwise into the coupling catch.

Figure 7:
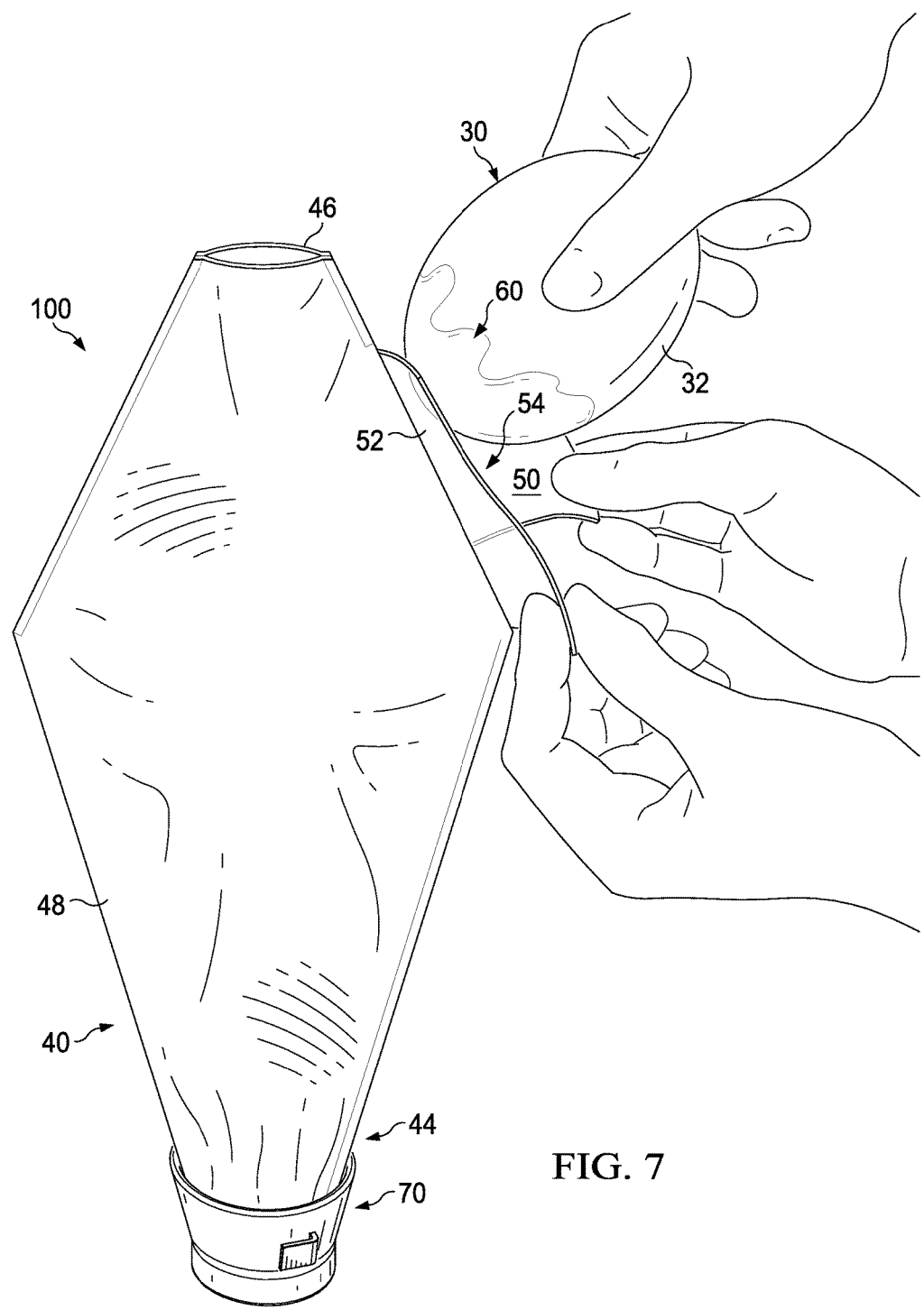

FIG. 7: Front perspective view of universal bellows with an implant being inserted through the prosthesis opening.

Figure 8:
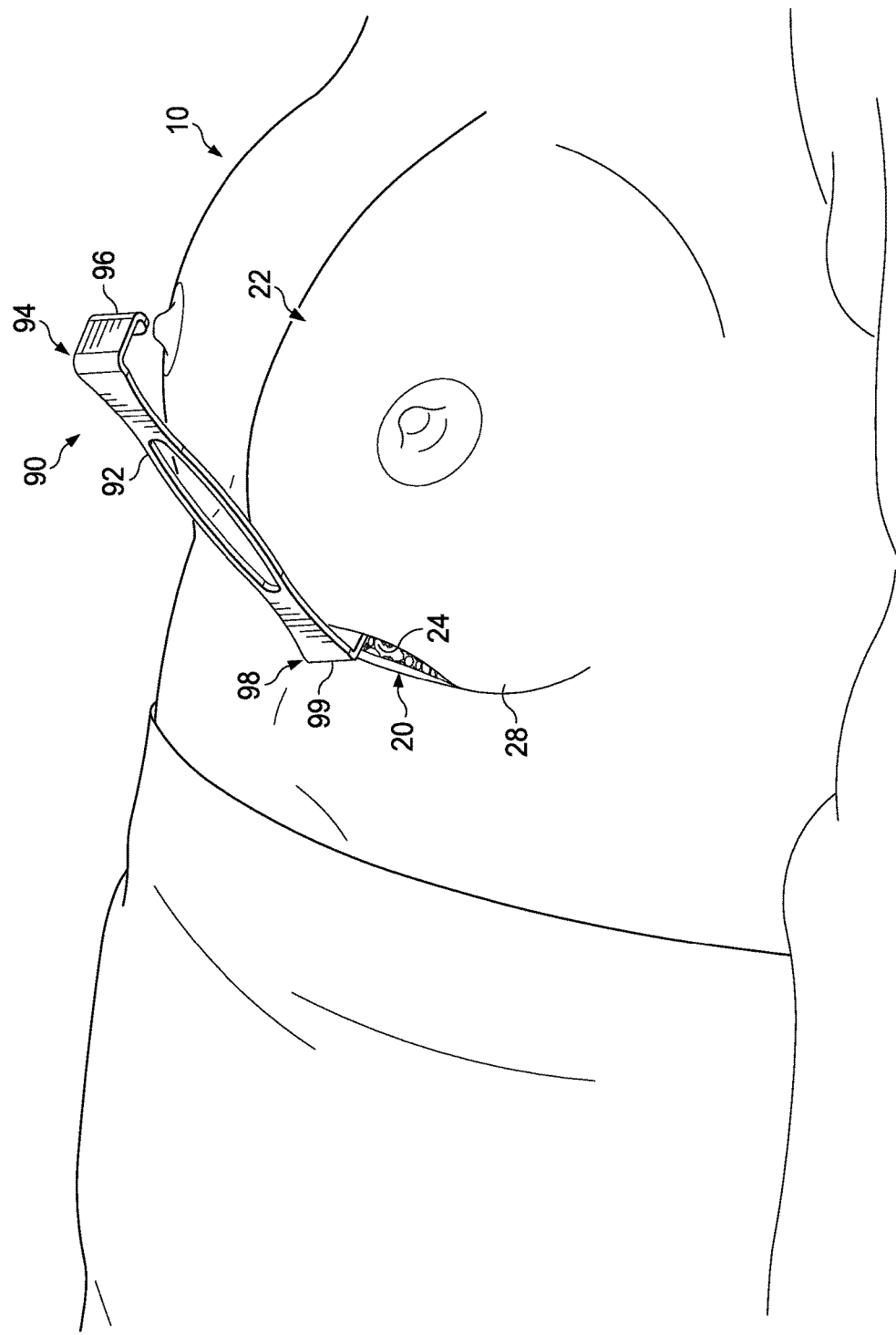

FIG. 8: Top front perspective view of the prior art showing a patient, incision, and retractor.

Figure 9:
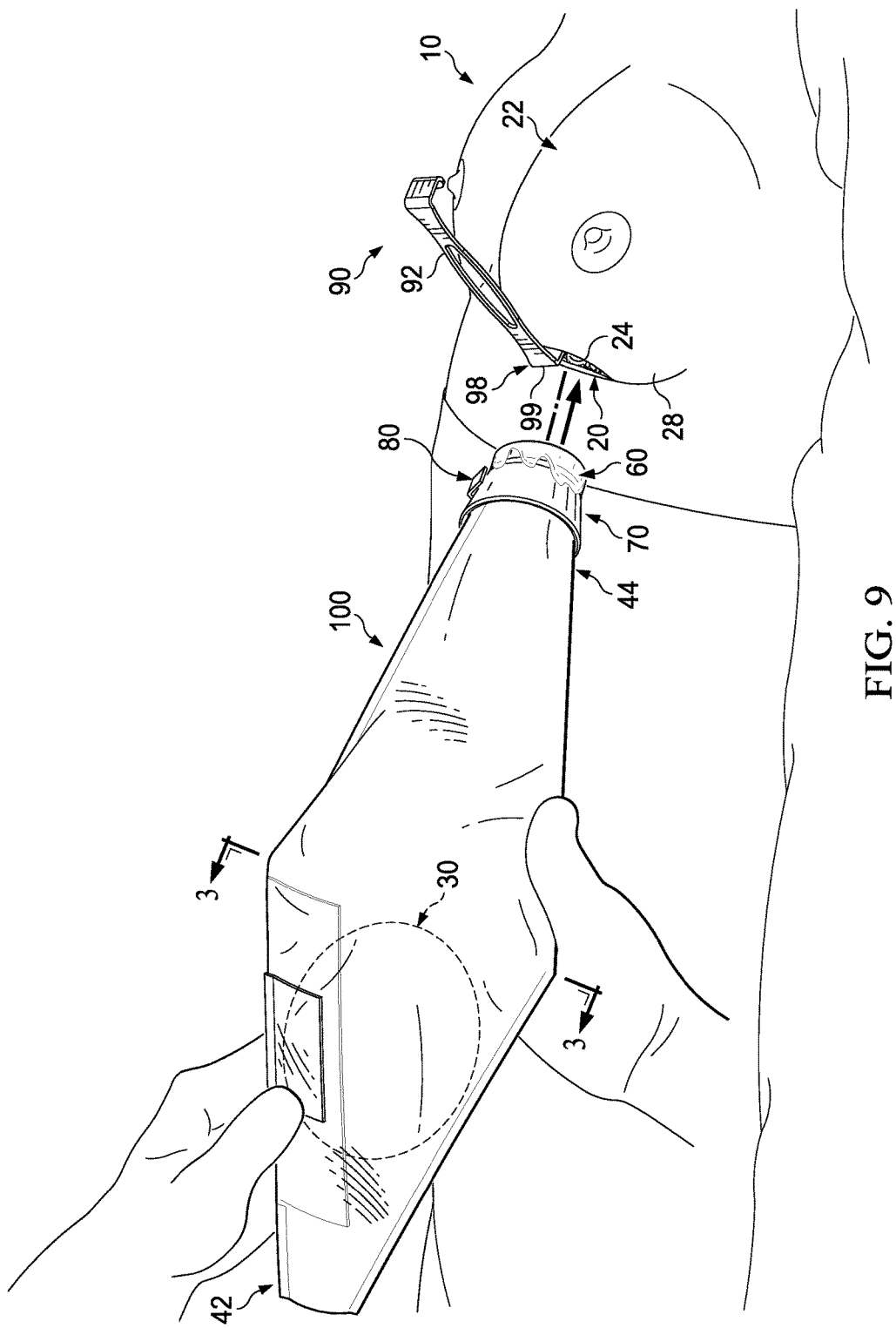

FIG. 9: Side perspective view of the universal bellows being inserted into the patient incision.

Figure 10:
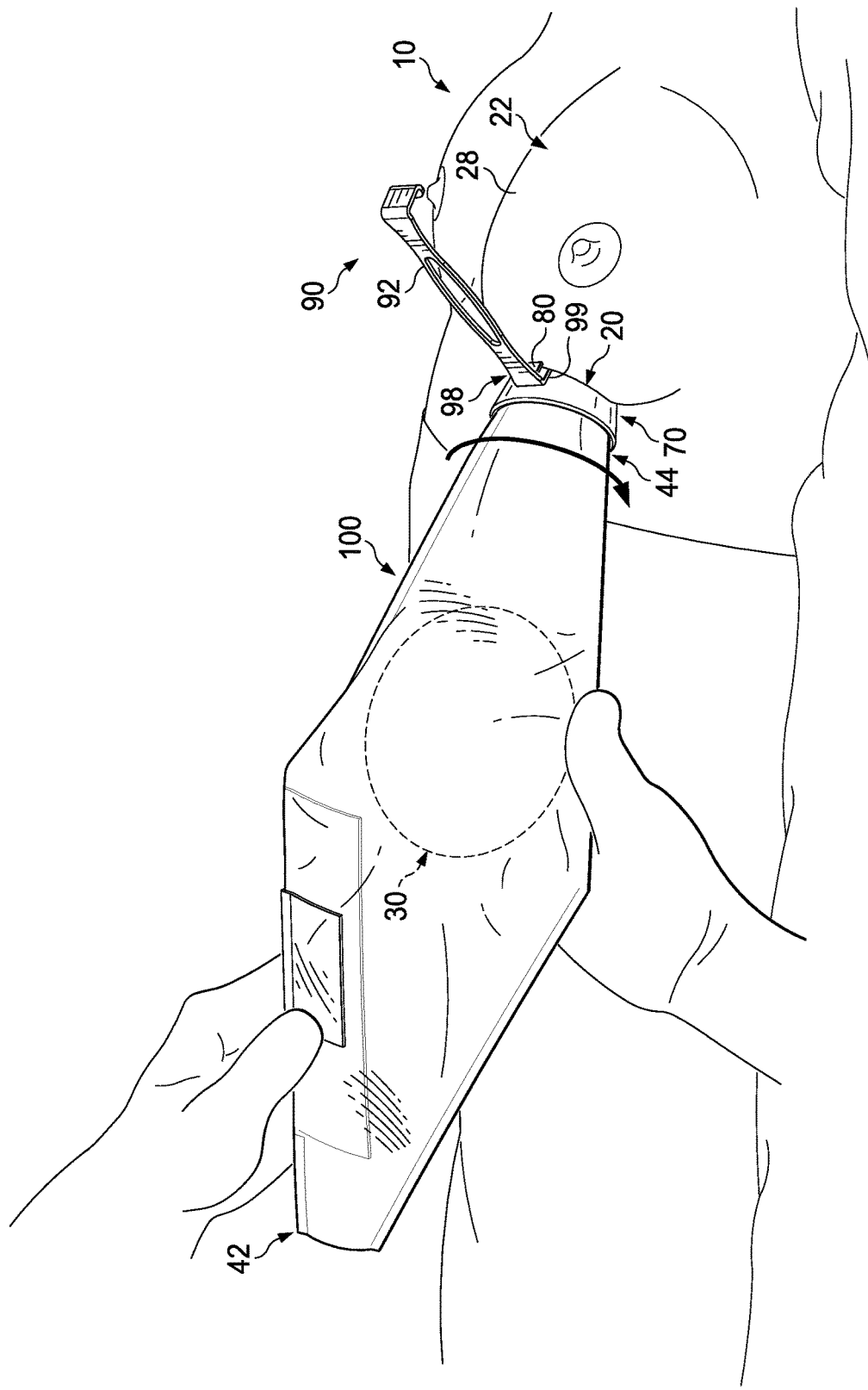

FIG. 10: Side perspective view of a universal bellows being rotated inside the incision.

Figure 11:
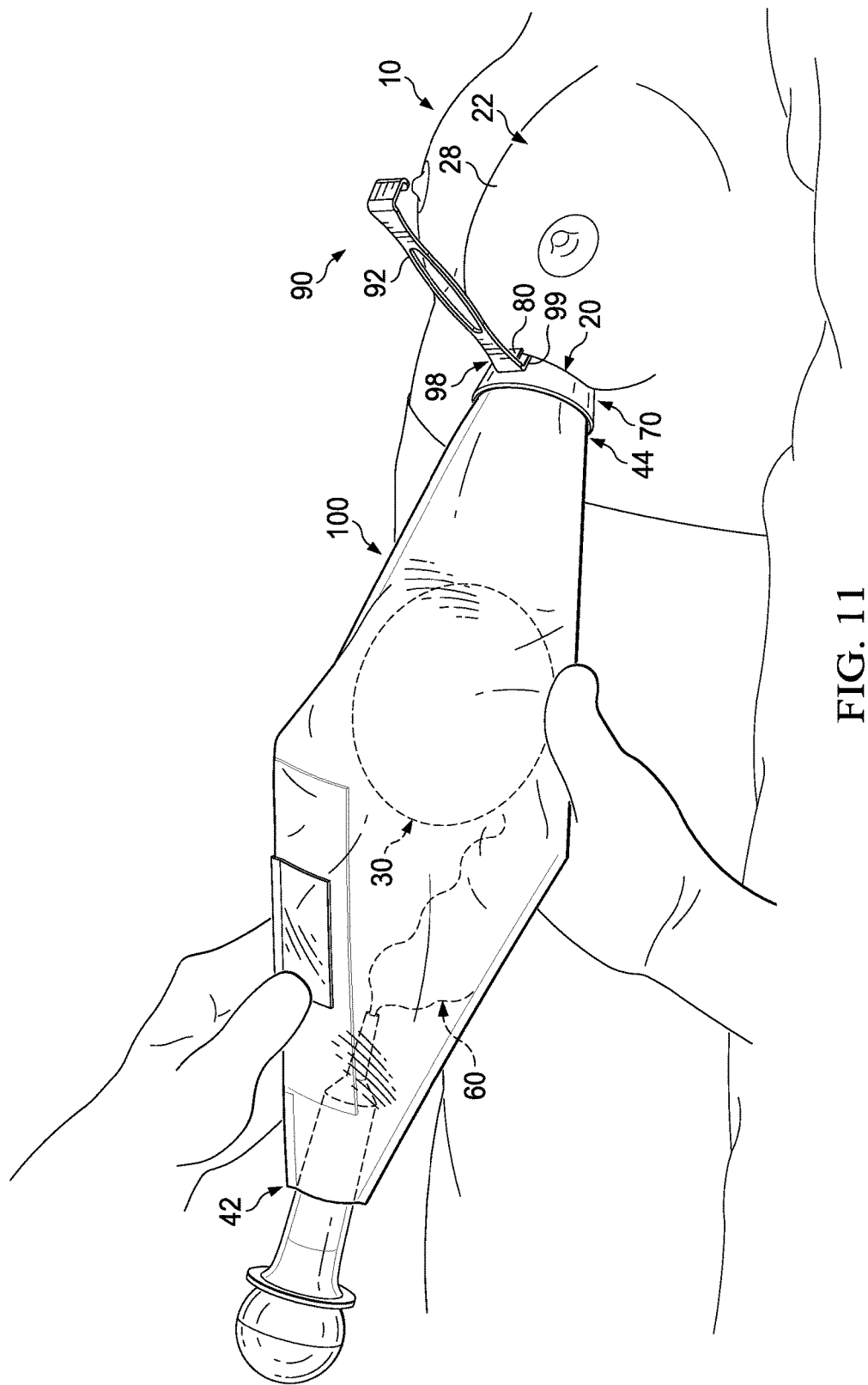

FIG. 11: Side perspective view of adding lubricant to the distal end of the bellows.

Figure 12:
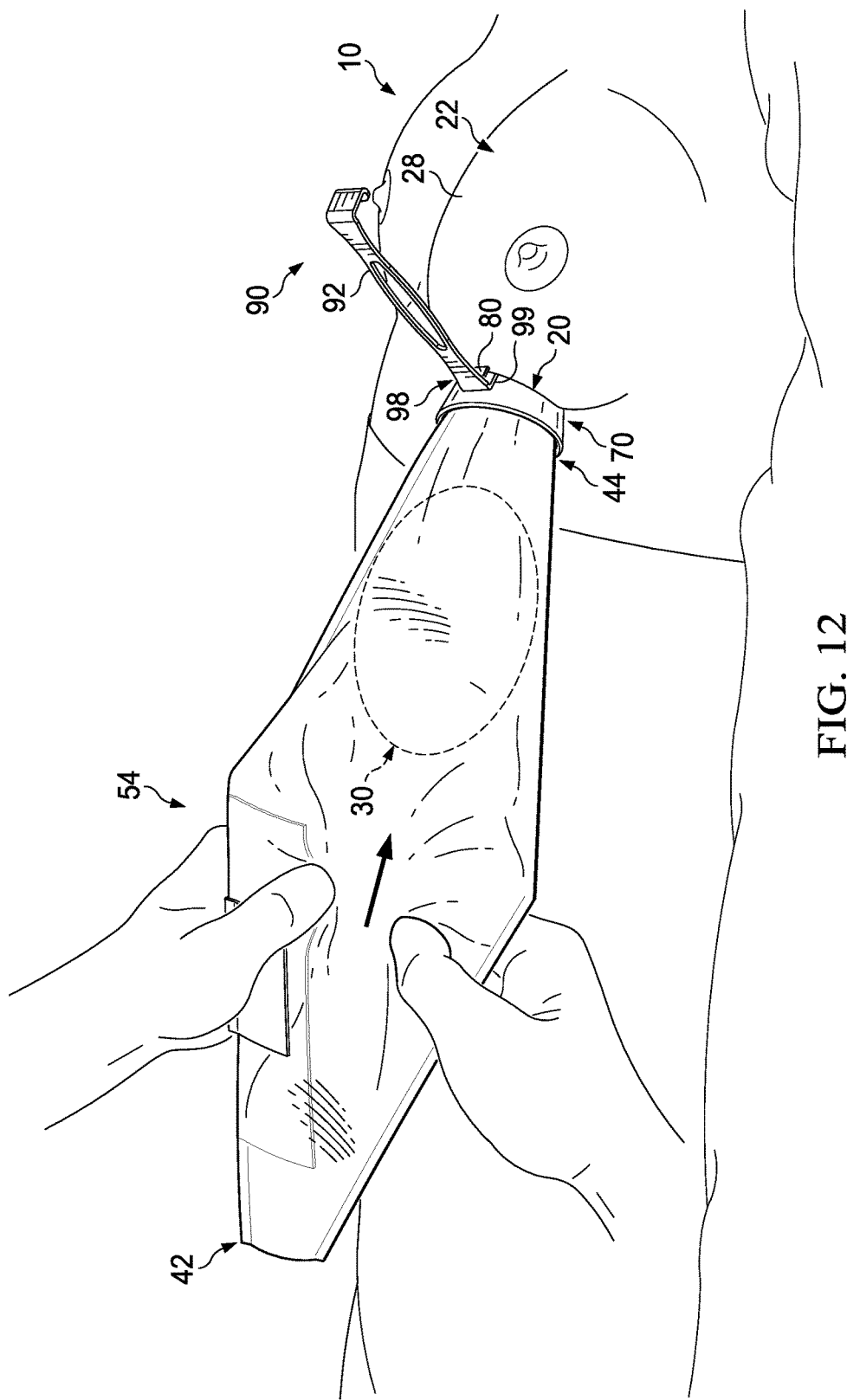

FIG. 12: Side perspective view of an implant being pushed and squeezed through the universal bellows.

KEY TERMS distal: the most distant portion from the point of attachment to the main body
inferior: closer to the feet
lateral: a position substantially located in any side of the longitudinal position of a patient's supine position
longitudinal: a lengthwise, or the longest, direction related to the patient's supine position
proximal: the closest portion from the point of attachment to the main body
superior: closer to the head of the body

REFERENCE NUMERALS IN DRAWINGS 10 patient
20 patient's incision, opening
22 patient's breast
24 patient's pocket
28 patient's skin tissue
30 prosthesis
32 breast implant
40 bellows device, bellows
42 bellows device distal end, distal opening
44 bellows device proximal end, proximal opening
46 bellows base fold
48 bellows initial fold
50 bellows exterior flap
52 bellows internal flap
54 bellows prosthesis opening
56 bellows seals
60 lubricant
70 universal device
72 universal distal end, distal opening
74 universal proximal end, proximal opening
80 universal catch
82 universal catch long segment
84 universal catch short segment
90 retractor
92 retractor handle
94 retractor handle distal end
96 retractor handle distal end lip
98 retractor handle proximal end
99 retractor proximal end lip
100 universal bellows

DETAILED DESCRIPTION OF THE DRAWINGS

Referring to the drawings, in which like numerals represent like elements,

FIGS. 1-4

FIGS. 1-4 identify individual elements of the universal bellows 100.

Turning to FIG. 1, the illustration depicting an unassembled bellows device 40. The bellows 40 form comprises two simple, convex, irregular hexagons folds 46, 48 with opposing flaps 50, 52. In a preferred embodiment, as shown in FIG. 1, the bellows base fold 46 is manufactured abutted against bellows initial fold 48 along the lower edge of the bellows initial fold 48 from its right most angle (RMA) to the bottom right angle (BRA). In a secondary embodiment, the bellows base fold 46 is manufactured abutted against the bellows initial fold 48 along the upper edge of the bellows initial fold 48 from its top right angle (TRA) to its right most angle (RMA). In a third embodiment the bellows initial fold 48 and bellows base fold 46 would be separately manufactured and assembled together at a later stage.

The bellows initial fold 48 has an internal flap 52 along the upper edge between the left most angle (LMA) to the top left angle (TLA). The bellows base fold 46 has an exterior flap 50 along the upper edge between the right most angle (RMA) to the top right angle (TRA).

A bellows 40 is made of a sheet material such as plastic or a flexible, surgical-grade nylon. The plastic may be strengthened or reinforced with fiber. The bellows 40 may be clear, or semi-transparent, in color to allow observation of the prosthesis 30 moving from bellows 40 into the patient pocket 24.

In the preferred embodiment, the bellows 40 would be folded along the lower abutted edge and manufactured with three bellows seals 56 along:
 a. initial fold's 48 TLA to the first edge of the internal flap 52;
 b. initial fold's 48 upper edge from the TRA to the RMA;
 c. initial fold's 48 lower edge from the LMA to the bottom left angle (BLA).

In the second embodiment, the bellows 40 would be folded along the upper abutted edge and manufactured with three seals 56 along:
 a. initial fold's 48 TLA to the first edge of the internal flap 52;
 b. initial fold's 48 lower edge from the RMA to the BRA;
 c. initial fold's 48 lower edge from the LMA to the (BLA).

In the third embodiment, the bellows 40 would be manufactured with separated initial fold 48 and based fold 46, stacked over each other and assembled with three seals 56 along:
 a. initial fold's 48 TLA to the first edge of the internal flap 52;
 b. initial fold's 48 upper edge from the TRA to the RMA;
 c. initial fold's 48 lower edge from the LMA to the BLA;
 d. initial fold's 48 lower edge from the RMA to the BRA;

The bellows seals 56 can be manufactured by glue, adhesive, heat bond, surgical tape or other coupling mechanism.

FIG. 2 shows the manufactured version of the bellows 40 once the bellows initial fold 48 is folded over the bellows base fold 46 and the abutted seam and the three seals 56 are completed. The manufactured bellows 40 comprises the bellows initial fold 48 partially sealed to the bellows base fold 46 so that it leaves a bellows distal opening 42, a bellows proximal opening 44, a bellows prosthesis opening 54, a bellows exterior flap 50 and a bellows internal flap 52. The bellows device distal end 42 is parallel to the bellows device proximal end 44. The bellows exterior flap 50 and bellows internal flap 52 would initially be presented to the surgeon with both flaps 50, 52 outside of the bellows 40 and surrounding the bellows prosthesis opening 54. The flaps 50, 52 may be of the same size; or different sizes to distinguish the exterior flap 50 from the internal flap 52.

To further illustrated the manufactured bellows 40, FIG. 3 shows a cross section of FIG. 9 with the bellows 40 containing a breast implant 32. With the prosthesis 30 in place, the bellows internal flap 52 is pushed through the bellows prosthesis opening 54 and the exterior flap 50 may be pushed over the top surface of the bellows initial fold 48. The exterior flap 50 may be sealed to the initial fold 48 with surgical tape, heat seal, instant glue, or other forms of seals. The seal 56 opposes the prosthesis opening 54 and joins the initial fold 48 and base fold 46.

In the preferred embodiment a liquid lubricant 60 surrounds the breast implant 32 inside the bellows 40. A coating of surgical lubricant 60 can be used on the inner surface of the bellows 40. As an alternative, the bellows 40 can be provided with a coating that becomes slick when wet. In still another alternative, the prosthesis 30 can be provided with a slick surface, such as a surgical lubricant 80. The lubricant 60 may also be an antibiotic solution.

Referring now to FIG. 4, the drawing shows a single catch 80 rotating universal device 70. A universal device 70 assembly is generally frusto-conical in shape and comprises a distal end and opening 72, a proximal end and opening 74, an "L"-shaped universal catch 80. The distal and proximal end 72, 74 have respective openings with the distal 72 opening being larger in diameter than the proximal end opening 74.

The proximal 74 portion of the device 70 can have a short section extending from the proximal end 74 toward a midpoint. The universal device 70 may have a constant inside diameter. Alternatively, the interior of the universal device 70 can have a sloped configuration from the distal end 72 to the proximal end 74.

The universal device 70 serves to stabilize the bellows 40, prevent the breast implant 32 from touching the patient skin tissue 28, and also serve to prevent damage to the implant 32 during the implant 32 insertion. The most important aspect of the universal device 70 is that it may be manufactured specifically for a certain breast implant 32 shape, volume, and diameter. This allows the manufacturer to specify the maximum outside pressure applied to the implant 32 during the insertion process. The manufacturer may also require a specific skin incision 20 length to allow insertion of the universal device 70 into the incision 20. The specifications take the burden off the surgeon to try to make shorter incisions 20. The proximal end of the universal device 74 can be manufactured to fit a single implant 32 size. To reduce the number of possible universal device 70 sizes, the manufacturer can also specify a universal device 70 would accommodate a range of implant 32 sizes.

In a preferred embodiment, the universal device 70 is shipped to the surgeon with the bellows 40 attached to the distal end 72 of the universal device 70. In another embodiment, the bellows device 40 is assembled to the universal device 70 by the surgeon. To assemble the universal bellows apparatus 100, the flexible bellows 40 is inserted into the universal device 70 and secured thereto. Double sided surgical tape can be used to couple the proximal end 44 of the bellows 40 inside of the universal distal end 72. Alternatively, the bellows 40 can be coupled to the universal device 70 by glue, adhesive, heat bonding or other coupling mechanism. In a third alternative, the proximal end of the bellows 44 may be pulled through the universal device 70 and then folding the proximal end of the bellows 44 over the proximal end of the universal device 74.

The universal device 70 has one universal catch 80 to attach to a retractor 90. The universal catch 80 is attached to the universal 70 by the universal catch short segment 84. The short segment 84 acts as a stop when the universal device 70 is rotated inside the patient's incision 20 into the retractor handle proximal end 98. The universal catch short segment 84 supports a perpendicular universal catch long segment 82. The long segment 82 holds the retractor 90 in a snug interference fit against the universal member 70.

FIGS. 5-12

FIGS. 5-12 show the operation of the universal bellows 100 to insert a prosthesis 30.

FIGS. 5 and 6 show the assembly of the retractor 90 removably into the universal bellows 100. The retractor 90 assembly comprises a handle 92 located in the center, a retractor handle distal end 94, retractor handle distal end lip 96, retractor handle proximal end 98, and retractor handle proximal end lip 99. The retractor 90 can have various shapes and sizes to match the particular application or surgeon preferences. The handle 92 of the retractor 90 is bent or angled on the ends 94, 98 relative to the intermediate portion. This is so that when the retractor 90 is coupled to the universal device 70, the retractor 90 extends laterally from the universal device 70, as shown in FIG. 5, so as not to interfere with the surgeon manipulating the universal bellows 100. The distal end 94 maybe be shorter, or longer, than the proximal end 98 and parallel to the handle 92. The ends 94,98 may be the same length and parallel to the handle 92. The retractor handle 92 is used for the insertion of the retractor 90 into the patient 10 and coupling the retractor 90 to the universal device 70 of the universal bellows 100. The proximal end 98 in the retractor 90 has a lip 99 that is angled relative to the end 98. The proximal end 98 of the retractor 90 form an interference fit with the universal catch 80. The retractor 90 is made of metal, such as stainless steel but can also be manufactured in a surgical plastic.

The retractor proximal end 98 is structured and arranged to be inserted through the incision 20 into a pocket 24 of a patient 10. The proximal end lip 99 helps maintain the proximal end 98 of the retractor 90 beneath skin tissue 28 of a patient 10. The universal device proximal end 74 is then placed into the patient's incision 20 so that the universal catch 80 remains outside of the incision 20.

The surgeon then rotates the universal device 70 until the universal catch long segment 82 forms an interference fit with the retractor 90, and the universal catch short segment 84 prevents further rotation, as in FIGS. 5-6.

Moving to the next drawing, FIG. 7, we show the insertion of the breast implant 32 by the surgeon and nurse into the universal bellows device 100. In the illustration, the bellows initial fold 48 and bellows base fold 46 have been attached along each bellows seal 56, the proximal end of the bellows 44 assembled into the distal opening 72 of the universal device 70, and the flaps 50, 52 are outside the universal bellows 100.

The surgeon has the option of applying a lubricant 60 to the prosthesis 30 directly before inserting into the universal bellows 100. The lubricant 60 may also act as an antibiotic solution. Then, separating the tabs 50, 52, the nurse opens the bellows prosthesis opening 54 and the surgeon slides the prosthesis 30 through the bellows prosthesis opening 54. The team would then fold the internal flap 52 into the bellows prosthesis opening 54 to prevent the breast implant 32 from moving back out of the opening 54. The exterior flap 50 may be left extended or folded over the bellows initial fold 48. If desired, the exterior flap 50 may be sealed to the initial fold 48 with surgical tape, heat seal or glue. In a preferred embodiment inserting the prosthesis 30 into the universal bellows 100 would be completed prior to inserting the retractor 90 into the patient incision 20. However, a surgeon could perform this step while the universal bellows 100 is inserted in the incision 20 and locked into the retractor 90.

FIG. 8 shows the patient 10 placed in a supine position and an incision 20 is made in the patient's skin tissue 28. In the figures, the incision 20 is made in the inferior breast 22 crease. With the incision 20 opened, the surgeon can then form a pocket 24 in one of two places under the breast 22: subglandular (between the breast 22 tissue and pectoralis muscle) or subpectoral (under the pectoralis muscle). The pocket 24 is then sized to receive the prosthesis 30. A retractor 90 is then inserted with retractor handle proximal end 98 and retractor proximal lip 99 used to retract the incision 20 and hold the incision 20 open. The surgeon opens the incision 20 by manipulating the retractor handle 92, retractors handle distal end 94, and retractor distal end lip 96.

The next step of inserting a breast implant 32 with a universal bellows 100 is shown in FIG. 9. With the proximal ends of the retractor 98 and proximal end lip 99 inserted into the incision 20 and located under the skin tissue 28 and moved to retract the incision 20, the universal device proximal 74 end may be lubricated with a lubricant 60 and inserted into the open incision 20 so that the coupling catch 80 rests above the skin tissue 28.

The universal bellows 100 is then rotated in FIG. 10 into the universal catch 80 until the catch 80 forms an interference fit with the retractor 90.

In FIG. 11, the surgical team inserts lubricant 60 in the distal end of the bellows 42. The liquid lubricant 60 surrounds the breast implant 32 inside the bellows 40 and may also be just an antibiotic solution.

Finally FIG. 12 shows the bellows 40 and prosthesis 30 are squeezed and/or twisted to force the prosthesis 30 toward the proximal end 44 of the bellows 40, proximal end of the universal device 74 and into the pocket 24. The prosthesis 30 deforms to fit through the universal device 70.

Once the prosthesis 30 is located inside the pocket 24, the retractor 90 is uncoupled from the universal device 70 by relative rotation between the universal bellows 100 and the retractor 90. The universal bellows 100 is then removed from the incision 20, followed by the retractor 90. The incision 20 can then be closed.

If the universal bellows 100 is designed for single use, they are disposed of. If universal bellows 100 is designed for reuse, they are subjected to sterilization procedures. An advantage of the universal bellows 100 and method is that the implant 32 and universal device 70 can be properly sized with respect to each other. A manufacturer of implants 32 can provide the properly sized apparatus 100 with the implant 32. The use of the universal device 70 acts as a sizing cuff on the end of the universal bellows 100. The size of the universal device 70 is matched to the size of the implant 32. For example, some implants 32 are physically large and require a universal device 70 with a larger diameter proximal and distal opening 74, 72, while other implants 32 are physically smaller and can use a universal device 70 with smaller openings 72, 74. By matching the universal bellows 100 to the size of the implant 32, the chance that the implant 32 will be damaged by excessive squeezing and stress is minimized. The implant 32 is subject to damage if the implant 32 is mishandled.

Possible mishandling includes subjecting the implant 32 to undue stresses or pressures, such as may be caused by attempting to squeeze the implant 32 through an opening 20 that is too small, and folding of the external silastic shell, internal fracture of the cohesive silicone gel. A surgeon may make an incision 20 in the patient 10 that is too small for the implant 32 and thus too much force is required to squeeze the implant 32 into the pocket 24. With the apparatus, the implant 32 is protected from damage by the provision of the properly sized universal device 70. A surgeon need not guess at what the proper size opening 20 should be for the specific implant 32. The major complication with implants 32 is capsular contracture thought to be due to sub-clinical infection. Sub-clinical infection is most likely caused by pushing the implant 32 through the skin incision 20, dragging natural skin 28 bacteria (still present after proper skin 28 preparations) into the pocket 24 surgically created for the implant 32. Use of this device 100 prevents the implant 32 from coming in contact with the skin tissue 28 during the insertion process.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

In the foregoing description, and the following claims, method steps and/or actions are described in a particular order for the purposes of illustration. It should be appreciated that in alternate embodiments, the method steps and/or actions may be performed in a different order than that described. Additionally, the methods described above may be embodied in machine-executable instructions stored on one or more machine-readable mediums, such as disk drives, thumb drives or CD-ROMs. The instructions may be used to cause the machine (e.g., computer processor) programmed with the instructions to perform the method. Alternatively, the methods may be performed by a combination of hardware and software. While illustrative and presently preferred embodiments of the invention have been described in detail herein, it is to be understood that the inventive concepts may be otherwise variously embodied and employed, and that the appended claims are intended to be construed to include such variations, except as limited by the prior art.

Benefits, other advantages, and solutions to problems have been described herein with regard to specific embodiments. However, the advantages, associated benefits, specific solutions to problems, and any element(s) that may cause any benefit, advantage, or solution to occur or become more pronounced are not to be construed as critical, required, or essential features or elements of any or all the claims of the invention. As used herein, the terms "comprises", "comprising", or any other variation thereof, are intended to cover a non-exclusive inclusion, such that a process, method, article, or apparatus composed of a list of elements that may include other elements not expressly listed or inherent to such process, method, article, or apparatus.

ADVANTAGES

From the description above, a number of advantages become evident for the "Universal Bellows." The present invention provides all new benefits for participating parties including manufacturers, patients and surgeons:

a) allows patients a lower risk of complications;
b) allows patients the smallest possible incision for a given implant;
c) allows doctors to prevent contamination by skin bacteria, gross infection and capsular contracture;
d) allows doctors an accurate and simplified tool for determining incision length;
e) allows doctors to eliminate damage to the implant during the insertion process;
f) allow manufacturer to predetermine incision length and thus removing burden off surgeon to make 'short' incision;
g) allows doctors a secure placement of the device within the incision;
h) allows doctors a simplified insertion process;
i) allows doctors to avoid a tearing of the proximal end of the device when applying pressure to the prosthesis.

The invention claimed is:
1. An apparatus for inserting a prosthesis through an incision into a surgical pocket, comprising:
 a. a prosthesis;
 b. a bellow comprising a bellows prosthesis opening, a proximal end and opening and a distal end and opening, the distal end opening being smaller than the proximal end opening, the bellows being semi-rigid and structured and arranged to receive the prosthesis through the bellows prosthesis opening located between the proximal end opening and the distal end opening;
 c. a universal device comprising a proximal end and opening and a distal end and opening, the distal end opening being larger than the proximal end opening;
 d. a universal bellows formed by assembling the proximal end of the bellows to the distal end of the universal device;
 e. a retractor that removably couples to the universal device, the retractor having a handle proximal end adjacent to the universal device proximal end opening and arranged to engage an edge of a surgical pocket opening, the handle proximal end being fixed relative to the universal device once the retractor is coupled to the universal device; and
 f. a universal device catch for removably coupling to the retractor, the catch having a short segment attached to the universal device and supporting a long segment.

* * * * *